United States Patent [19]

Swanson et al.

[11] Patent Number: 5,784,352

[45] Date of Patent: Jul. 21, 1998

[54] APPARATUS AND METHOD FOR ACCESSING DATA ON MULTILAYERED OPTICAL MEDIA

[75] Inventors: Eric A. Swanson, Acton; Stephen R. Chinn, Westford, both of Mass.

[73] Assignee: Massachusetts Institute of Technology, Cambridge, Mass.

[21] Appl. No.: 916,759

[22] Filed: Aug. 19, 1997

Related U.S. Application Data

[63] Continuation of Ser. No. 492,738, Jul. 21, 1995, abandoned.

[51] Int. Cl.$^6$ .................................................. G11B 7/00
[52] U.S. Cl. ...................... 369/94; 369/100; 369/112; 369/54; 369/275.2
[58] Field of Search .......................... 369/100, 109, 369/108, 103, 112, 116, 93, 94, 275.1, 275.2, 275.3, 275.4, 283, 284, 286, 53, 54, 47, 48, 58, 59

[56] References Cited

U.S. PATENT DOCUMENTS

| | | | |
|---|---|---|---|
| 3,905,703 | 9/1975 | Matsumoto | 356/106 R |
| 3,912,391 | 10/1975 | Fleisher et al. | 355/54 |
| 4,969,142 | 11/1990 | Nagashima et al. | 369/112 X |
| 5,097,464 | 3/1992 | Nishiuchi et al. | 369/112 |
| 5,121,376 | 6/1992 | Kuder et al. | 369/100 |
| 5,218,594 | 6/1993 | Tanno | 369/100 |
| 5,251,198 | 10/1993 | Strickler | 369/110 |

FOREIGN PATENT DOCUMENTS

| | | | |
|---|---|---|---|
| 0446063 A1 | 9/1991 | European Pat. Off. | G11B 7/24 |
| 0511023 A1 | 10/1992 | European Pat. Off. | G11B 7/00 |
| 61-227237 | 10/1986 | Japan | G11B 7/135 |
| 61-240447 | 10/1986 | Japan | G11B 7/135 |
| 7049306 | 2/1995 | Japan | G01N 21/45 |

OTHER PUBLICATIONS

"Development of High Density 3-D Optical Disc Technology", Eric Swanson, Massachusetts Institute of Technology, pp. 1–11, not dated.

"Multilevel Volumetric Optical Storage", Kurt A. Rubin, et al., *SPIE, Optical Data Storage*, vol. 2338, pp. 247–253, 1994.

"Samsung gets behind Toshiba DVD effort", David Lammers, *Electronic Engineering Times*, p. 1, newspaper article, not dated.

"A long road to overnight success", *Management/New Products*, pp. 60–66, not dated.

"Multiwavelength, Multilevel Optical Storage Using Dielectric Mirrors", John R. Wullert II, et al., *IEEE, Photonics Technology Letters*, vol. 6, No. 9, pp. 1133–1135, Sep. 1994.

"Rewritable optical disk drive also reads CD-ROMs", Yvonne A. Carts, *Laser Focus World, Design and Applications*, p. 115, Jan. 1995.

"Technology Roadmap", *Optoelectronic Technology Roadmap Conclusions & Recommendations*, Optoelectronics Industry Development Association, Apr. 15, 1994, pp. iii–vii—1–63.

(List continued on next page.)

*Primary Examiner*—Muhammad N. Edun
*Attorney, Agent, or Firm*—Testa, Hurwitz & Thibeault, LLP

[57] ABSTRACT

Apparatus and methods for accessing data on a multilayered optical storage medium. The apparatus uses the time-of-flight of illumination directed to and reflected by the layers of the optical medium to access data stored on a desired layer of the medium. More particularly, alterations in illumination reflected from the desired layer are detected to access data stored on the layer. In accordance with embodiments of the invention utilizing interferometric techniques, the time-of-flight of a reference illumination is adjusted to cause interference of the reference illumination with the illumination reflected from the layer which contains the data to be accessed. Alternatively, and in accordance with embodiments of the invention utilizing non-interferometric techniques, the time-of-flight of illumination reflected by the layer which contains the data to be accessed is selected to permit data stored on the desired layer to be accessed.

54 Claims, 9 Drawing Sheets

OTHER PUBLICATIONS

"*High–speed optical coherence domain reflectometry*" E.A. Swanson, et al., Optical Society of America, pp. 151–153, 1992.

"*In vivo retinal imaging by optical coherence tomography*", E.A. Swanson, et al., Optical Society of America, pp. 1864–1866, 1993.

"Optical storage: a growing mass market for lasers", Bill Lenth, *Laser Focus World*, pp. 87–91, Dec. 1994.

"Optical Tomography", Kristin Leutwyler, *Scientific American*, pp. 147–149, Jan. 1994.

"Optical Coherence Tomography", David Huang, et al., *Science*, American Association for the Advancement of Science, vol. 254, pp. 1178–1181, Nov. 22, 1991.

International Search Report dated Sep. 13, 1996 from corresponding PCT Application No. PCT/US96/05627.

APPARATUS AND METHOD FOR ACCESSING DATA ON MULTILAYERED OPTICAL MEDIA

This is a continuation of application Ser. No. 08/492,738 filed on Jul. 21, 1995 now abandoned.

GOVERNMENT SUPPORT

This invention was made with government support under Contract Number F19628-95-C-0002 awarded by the U.S. Air Force. The government has certain rights in the invention.

FIELD OF THE INVENTION

This invention relates to devices and techniques for accessing data on storage media and more specifically for accessing data on multilayered optical storage media.

BACKGROUND OF THE INVENTION

Optical storage media used in audio compact-disk (CD), video disk and computer (CD-ROM) technologies have the ability to store very large amounts of data in a very small area at a very low cost per bit of data stored. These factors, in addition to the very rapid data access times obtainable from optical storage media and the ease by which such media is replicated, combine to make optical storage media a preferred media for storing data in the foreseeable future.

Referring to FIG. 1, an optical data storage system 10 known to the art typically includes an optical storage medium 14 and a device 18 to access data on the medium. The optical storage medium 14 includes a layer of storage material upon which data is encoded, for example by the presence or absence of pits 24 or depressions in the storage medium 14. The device 18 to access this data typically includes a laser light source 22 which is directed toward the storage medium 14 and a photodetector 26 which detects light reflected from the storage medium. Portions of the storage medium upon which data is encoded reflect the incident laser light 30 in a manner different than portions of the storage media 14 upon which no data is encoded. For example, pits 24 indicating the presence of data reflect the incident laser light 30 to a lesser or greater degree than the portions of the storage medium 14 without the data pits 24. The photodetector 26 detecting the amount of reflected light 34 from the storage medium 14 thus generates a signal which corresponds to the data encoded on the storage medium 14.

The success of such single layer optical storage technology has led to research in multilayer optical storage media and devices in order to further increase the amount of data stored on a single storage unit, such as a CD-ROM. One such attempt at multilayer optical storage utilizes a short depth of field focusing lens in the path of the incident laser light. By moving the focusing lens toward and away from the medium, it is possible, by focussing, to select one layer of the multilayer optical medium for access. Such a system has been able to access data written in layers separated by distances on the order of 100 μm.

Another method of increasing the density of optical data storage is disclosed in U.S. Pat. No. 5,218,594 to Tanno. In this patent, data is stored as a series of refractive index discontinuities within a waveguide. An interferometer selects which of the series of discontinuities within the waveguide is to be accessed by introducing light into the waveguide through the end of the guide. Many such waveguides are aligned in parallel to thereby form a three dimensional medium in which data is stored vertically in each individual waveguide. Replication of such waveguides would likely require a long and expensive process, as compared to conventional embossing and coating methods.

The present invention relates to systems and methods for improved multilayer storage and detection of data on an optical storage medium which can be replicated in a commercially feasible manner.

SUMMARY OF THE INVENTION

In accordance with the invention, apparatus and methods are provided for accessing selected layers of data stored on an optical storage medium. The data may be stored on multiple layers of a multilayered medium or alternatively, may be stored on multiple layers within a unitary optical medium.

In the case of a multilayered medium, the medium is partially transparent so as to permit a beam of incident illumination to impinge upon all layers of the medium. The apparatus uses the time-of-flight of illumination reflected by the layers of the medium to select a desired layer for access. More particularly, alterations in the light reflected by the layers and caused by data recorded on the layers of the optical storage medium are detected as data. Illustrative alterations of the reflected light are reflectivity which, in some cases may be detected based on the absence or presence of a reflection, light polarization, or spectral alterations of light.

In accordance with embodiments of the invention utilizing interferometric techniques, the time-of-flight of a reference illumination is adjusted to cause interference with the reflections from a desired layer of the medium to thereby select the layer having data to be accessed. Alternatively, in accordance with embodiments utilizing non-interferometric techniques, the time-of-flight of illumination reflected by a desired layer is measured to select the desired layer upon which data is to be accessed.

An additional feature of the invention includes the use of a Fabry-Perot arrangement for reducing the effect of out-of-plane jitter of the optical medium on the data detection process. Also described is apparatus and techniques for simultaneously accessing multiple layers of a multilayered disk and apparatus for detecting multiple bits/pixel in single or multi-layered disks.

BRIEF DESCRIPTION OF THE DRAWINGS

This invention is pointed out with particularity in the appended claims. The above and further advantages of this invention may be better understood by referring to the following description taken in conjunction with the accompany drawings, in which:

DESCRIPTION OF THE PREFERRED EMBODIMENT

Figure 2:
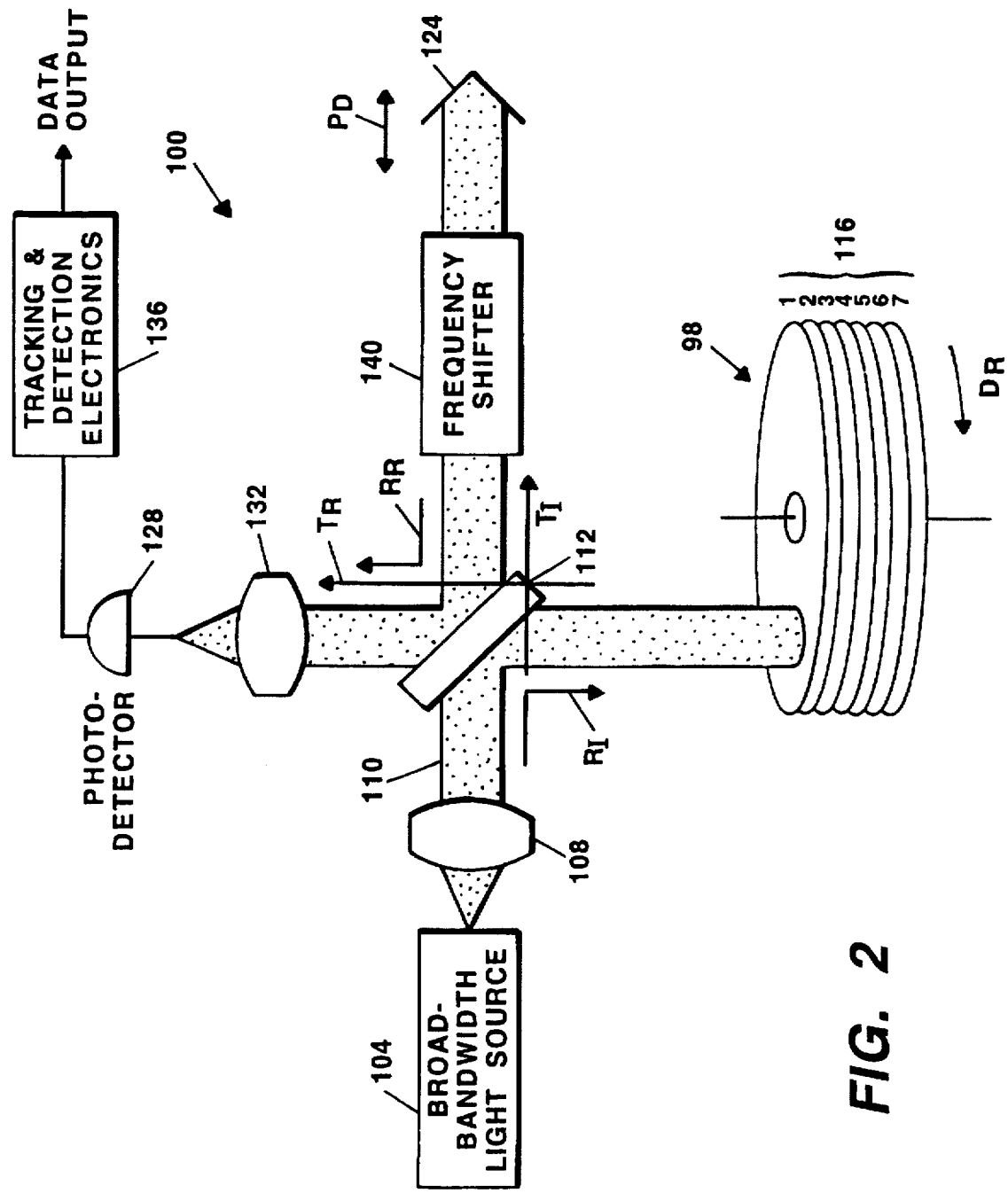
FIG. 2 is a block diagram of an embodiment of the apparatus of the invention utilizing an interferometric technique.

Referring to FIG. 2, one embodiment of apparatus for accessing data from a multilayered optical medium, such as an optical medium 98, includes a Michelson interferometer 100 and a broad-bandwidth light source 104. Light from the broadband light source 104 is collimated by a lens 108 into a beam 110 and transmitted to a beam splitter 112 which, in this embodiment, is a partially transparent mirror. The beam splitter 112 splits the incident beam 110 into two portions, one of which is reflected (arrow R) toward the medium 98 and one of which is transmitted (arrow T) through the beam splitter 112 toward a movable mirror 124.

In the illustrative embodiment of FIG. 2, the multilayered optical medium 98 is a disk 116 having seven layers, as shown. Although the various embodiments of the present invention are described generally in terms of accessing data stored on a layer of a multilayered optical disk, other forms of multilayered optical media, such as an optical tape, may also be used. Moreover, the data may alternatively be stored on multiple layers of a unitary optical medium.

Data may be written on the disk 116 in several ways. In the simplest embodiment, permanent data is embossed in sequential layers in a fashion similar to that used for a single layer in a conventional CD or CD-ROM. The major difference in the present embodiment is that no highly reflective metal film is applied to enhance the reflectivity of the data layer. In one embodiment, a data pattern is embossed on the surface of a transparent (e.g. polymer) layer. Another thin transparent layer, having a different refractive index, is applied on top of the first data pattern and the next data pattern is embossed on the new surface, without disturbing the first data pattern. Additional layers and data are added in similar fashion. The difference in refractive indices at each data interface causes the reflected signal, which is altered by the presence of a data depression (bit). In another embodiment, permanent data bits at each layer may be formed by sequential thin-film deposition and photolithographic patterning from masks containing the data patterns.

To create multi-layer erasable (READ/WRITE) data requires auxiliary higher power beams that can locally heat or otherwise modify the selected data interface and either change the material phase and alter the reflectivity or modify the magnetization of a magneto-optic layer, thereby modifying the polarization of reflected light. To select the data layer for modification requires either an interferometric or time-of-flight coincidence of WRITE pulses. For example, in one embodiment a WRITE sequence consists of a pair of pulses, separated in time such that the first pulse penetrates all the data layers, is reflected by a final high reflectance layer, and coincides with the second pulse at the desired depth. The pulse energies are such that both are required to be coincident in order to modify the data layer. The pulse times must be short enough to achieve the desired depth resolution.

The multilayered disk 116 reflects the incident light and the reflected light (arrow $T_R$) is transmitted through beam splitter 112 and a focusing lens 132, to a detector 128. The detector 128 is connected to tracking and detection electronics 136 which provide data output indicative of data stored on the disk 116. Light reflected by the movable mirror 124 is reflected by the beam splitter 112 (arrow $R_R$) through focussing lens 132 and to detector 128. An optional frequency shifter 140 is positioned between the beam splitter 112 and the movable mirror 124 and provides a shifting of the frequency of light passing through it. The purpose of the frequency shifter 140 is to increase the signal to noise ratio of the data output signal, by moving the interference signal away from noise associated with baseband detection. Illustrative types of frequency shifters suitable for use with the present invention are serrodyne shifters, phase modulators and acousto-optic modulators.

The measuring path of the interferometer 100 is defined as the path from the source 104, reflected (arrow $R_I$) by the beam splitter 112 toward the disk 116, reflected by the disk 116 and transmitted (arrow $T_R$) through the beam splitter 112 to the detector 128. The reference path is defined as the path from the source 104 transmitted (arrow $T_I$) through the beam splitter 112 to the movable mirror 124, reflected by the mirror 124 and reflected (arrow $R_R$) by the beam splitter 112 toward the detector 128. When the length of the reference path equals the length of the measuring path, an interference pattern is generated at the detector 128. Thus, by moving (arrow $P_D$) the movable mirror 124, the length of the reference path is adjusted to insure that an interference pattern is generated by the interference of the reference beam with the beam reflected from a selected layer of the multilayered disk 116. In this way, the time-of-flight of the reference light beam is adjusted in order to select a desired layer of the multilayer disk 116 for access.

Figure 1:
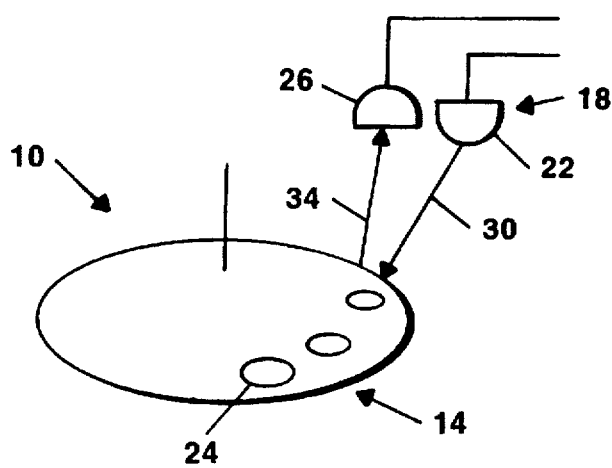
FIG. 1 is a block diagram of an optical storage medium and data access device known to the prior art.
Figure 3:
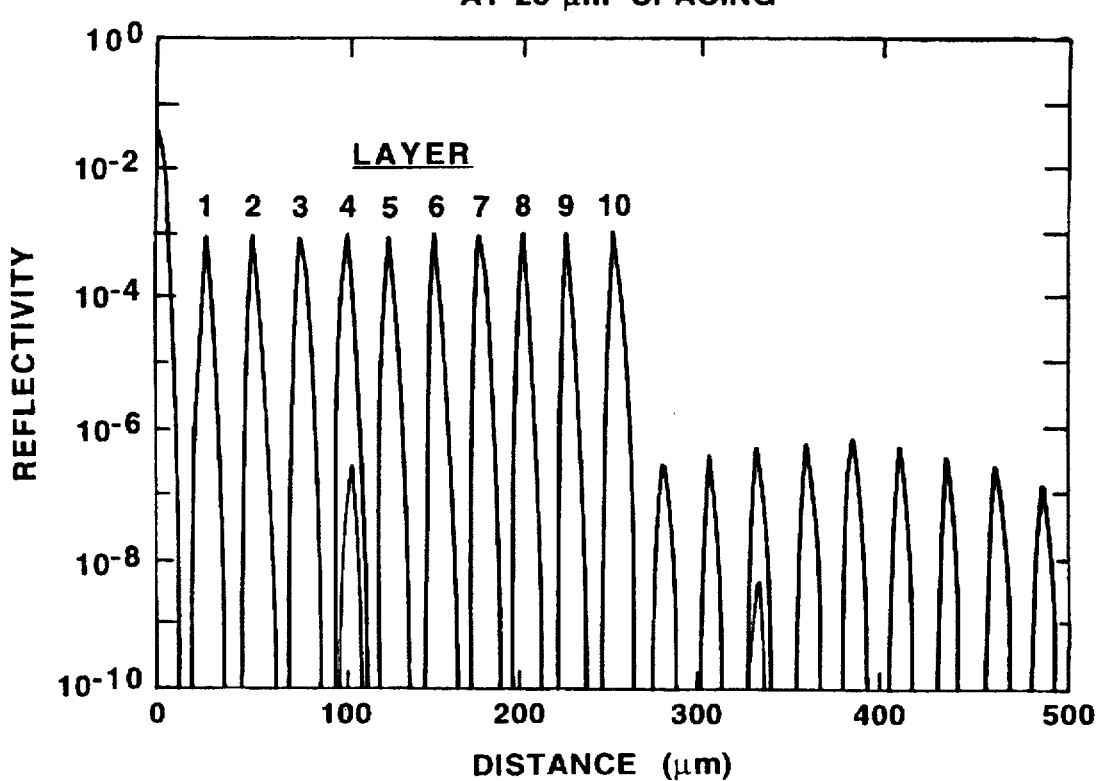
FIG. 3 is a graphical representation of illustrative reflectivity levels of light reflected by layers of a multilayered optical medium as a function of the distance into the disk from the top disk surface.

Referring also to FIG. 3, coherent reflectivity of light reflected by various layers of the disk 116 is graphically depicted as a function of the distance into the disk from the top disk surface. In this example, the layers of the multilayered disk 116 are separated by 25 μm and the central wavelength of the incident light is 920 nm. The signal in FIG. 3 may be thought of as being generated by a scan of the reference mirror 124, so that the interference signal has a local maximum when the reference mirror optical path length sequentially matches the optical path length of each data layer.

Figure 9:
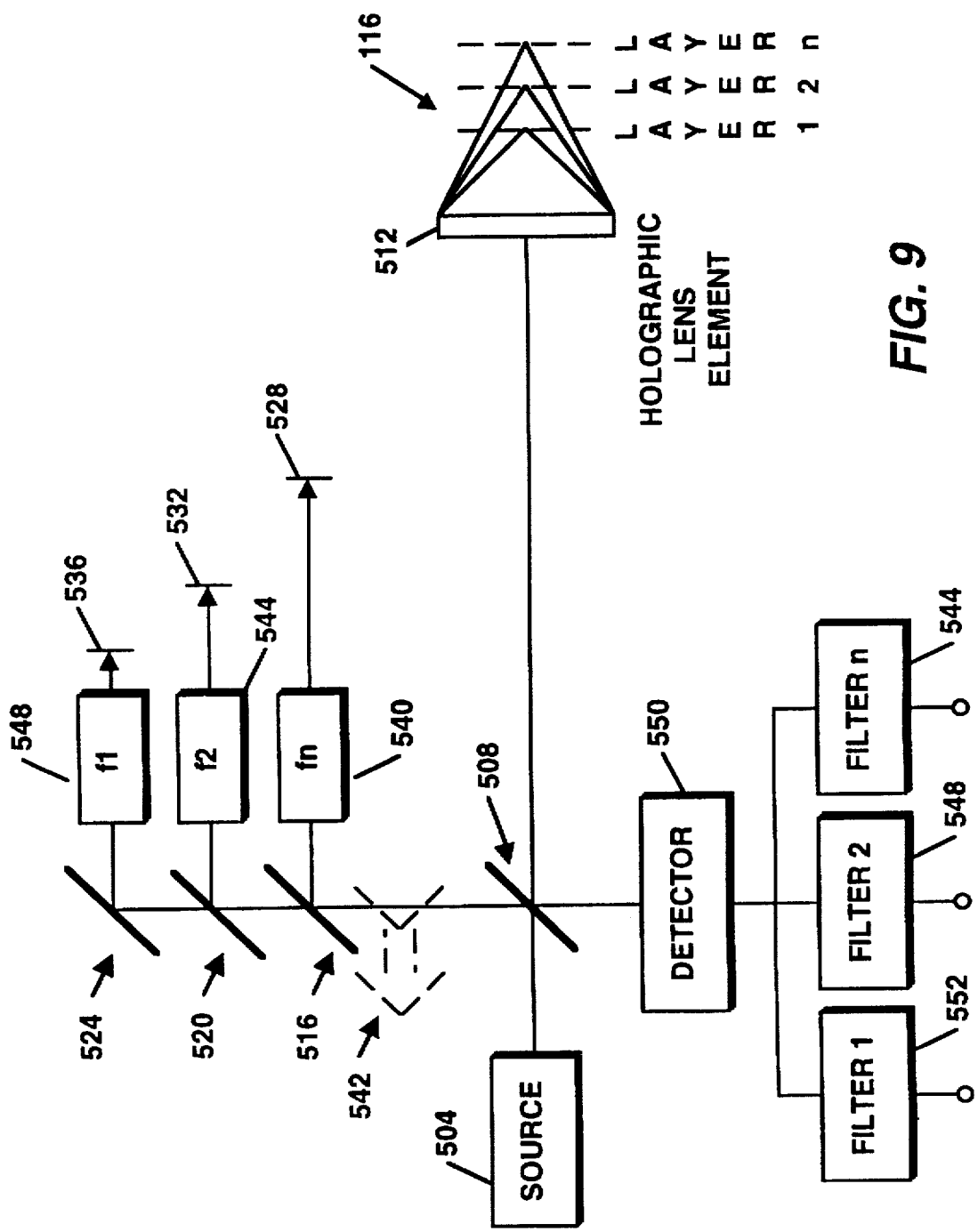
FIG. 9 is a block diagram of an interferometric embodiment of the invention for simultaneously detecting data on multiple layers of an optical medium.

In one embodiment of the invention, one reference path length at a time is chosen to select a given data layer, and the signal from the selected layer varies in accordance with the presence or absence of a data bit (i.e., layer #4 in FIG. 3). In another embodiment of the invention, the signals from all the layers may be detected simultaneously if a separate means of distinguishing among the layers is imposed. One such example is shown in FIG. 9, in which multiple reference paths, each one corresponding to a respective data layer, are provided and the frequency of the reference light for each layer is shifted by a different amount. The resulting interference signals from each layer would then occur at distinct heterodyne beat frequencies, allowing the data from all layers to be detected simultaneously and distinguishably.

Figure 4:
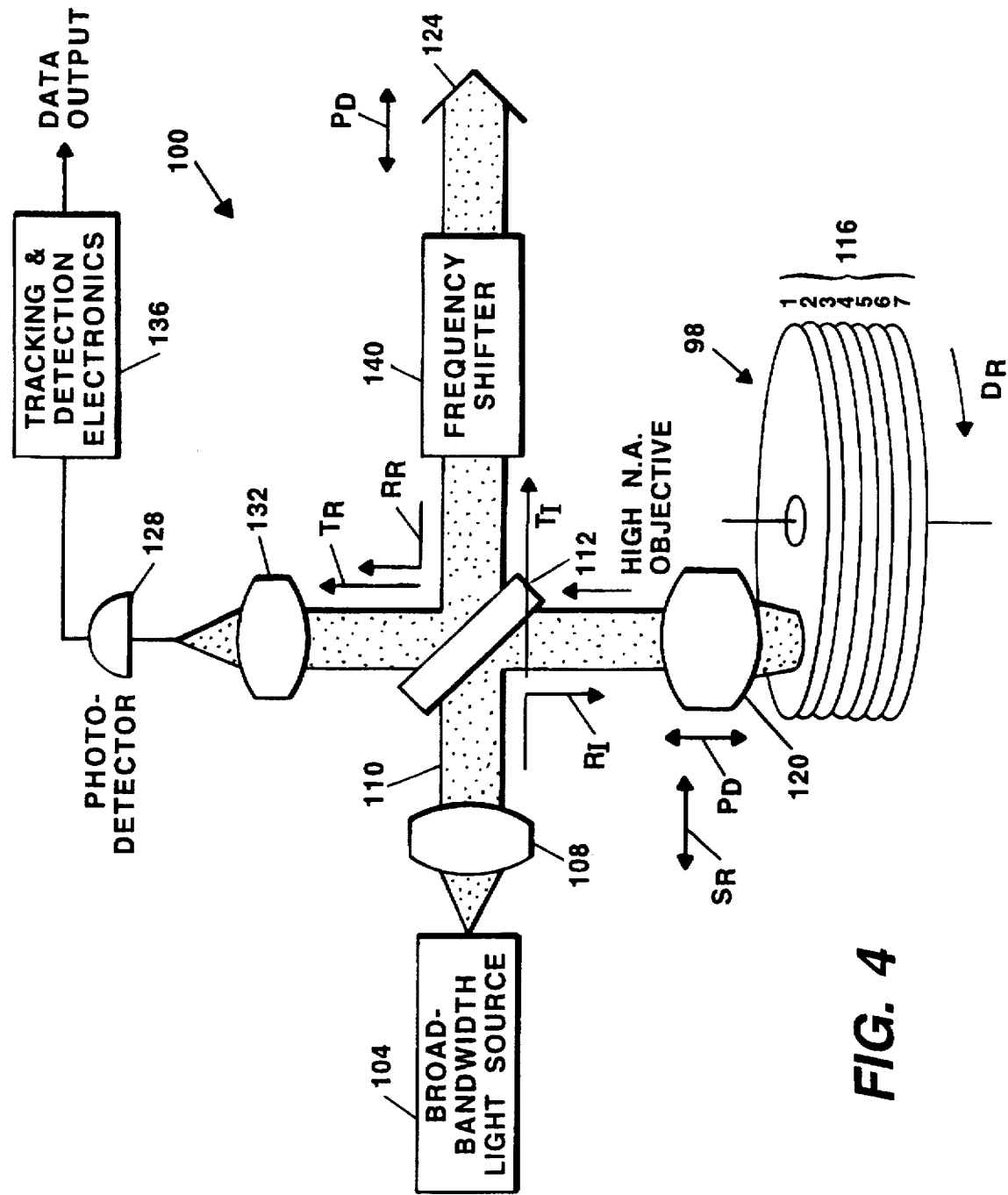
FIG. 4 is a block diagram of the apparatus of FIG. 2 including a high numerical aperture lens.

Referring to FIG. 4, an additional improvement to the system of FIG. 2 may be achieved by incorporating a high numerical aperture lens 120 in the light path to the optical medium 98. By moving the lens 120 toward and away from the disk layers (along arrow $F_D$), different layers may be brought into focus. In this way, light may be focussed by the lens 120 onto and reflected from a specific, desired layer of the multilayer disk 116, thereby enhancing the ability of the system to discriminate between layers and maximizing the areal density of each layer.

As the disk 116 rotates (arrow $D_R$) and the interferometer 100 translates radially (arrow $S_R$) with respect to the disk 116, substantially all portions of the surface of the disk 116 may be brought beneath the lens 120. Therefore, by moving the movable mirror 124, rotating the disk 116 and radially translating the interferometer 100, substantially the entire surface of all layers of the multilayer disk 116 may be accessed.

Tracking of the data can be done using means similar to a conventional disk system. For example, tracking may be achieved with the use of tracking data provided on the medium for tracking purposes. Astigmatic lens or knife-edge sensors can track focus errors, and detection of side-diffracted beams can be used for lateral tracking. Such sensing can be done with a multi-element optical intensity detector (e.g. quad-cell photodiode). The optical field used for this tracking is the combined signal and reference, so the same interferometric beams used for detecting data are used for tracking. The only additional tracking requirement for interferometric detection is to maintain track of the reference optical path length with that of the selected data layer. This may be accomplished by imposing a small, low-frequency dither on the reference mirror and using standard feedback techniques with the low-frequency component of the detected signal. Other servo techniques are also possible.

Figure 5:
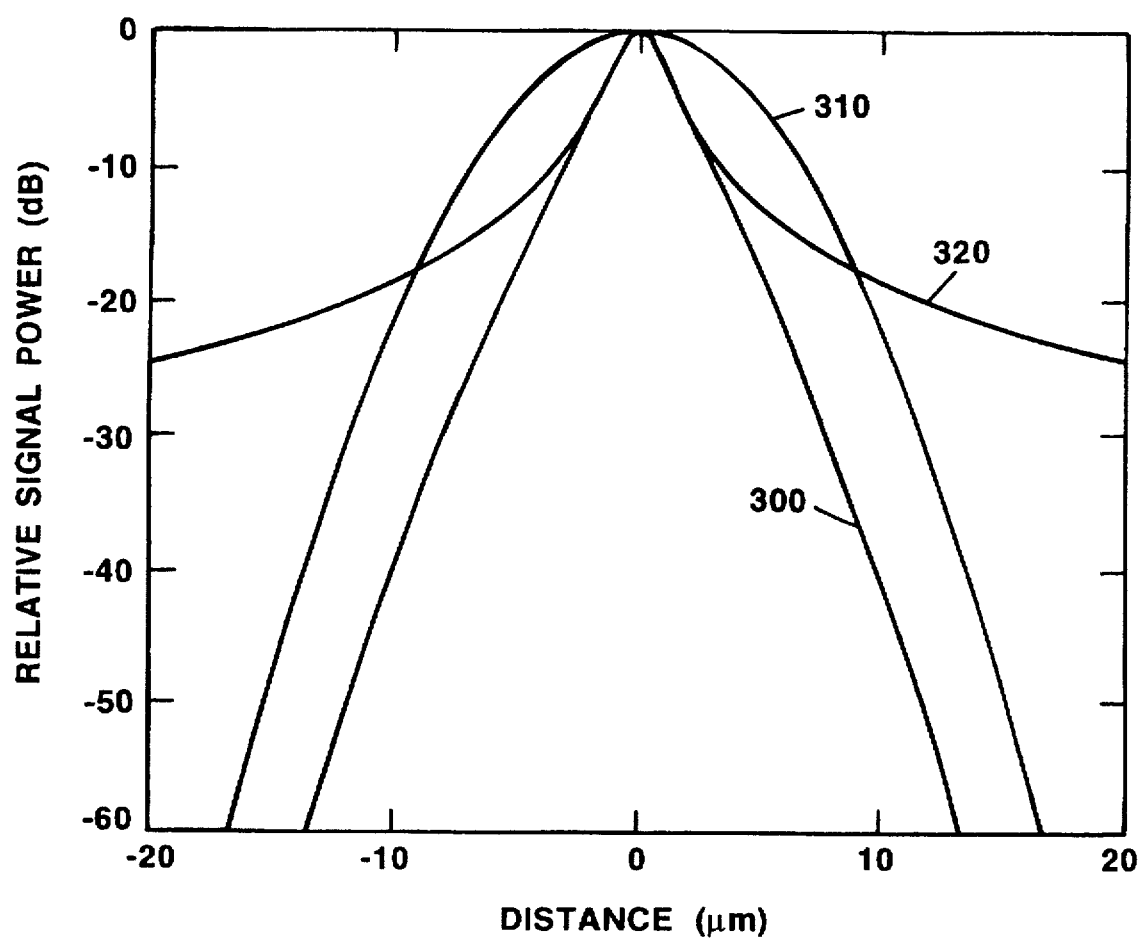
FIG. 5 is a graphical representation of the point-spread functions of a lens focussing system, the interferometric system of FIG. 2 and the combination interferometric and lens focusing system of FIG. 4.

Referring also to FIG. 5, the longitudinal point-spread function for the apparatus of FIG. 2 is shown by curve 310 and the longitudinal point-spread function for the apparatus of FIG. 4 is shown by curve 300. Also shown in FIG. 5, by curve 320, is the longitudinal point-spread function for a lens only system (not shown). As can be seen, the use of the combination of lens 120 and interferometer 100 (curve 300) permits higher resolution than either the interferometer 100 alone (curve 310) or a lens system alone (curve 320) and thus, reduces cross-talk between layers and enables closer layer spacing and a larger number of layers than is possible with the lens system alone.

Referring to FIGS. 3 and 5, it can be seen that the system utilizing the lens and interferometer (curve 300) has a larger dynamic range and better signal-to-noise ratio for weakly or moderately reflecting data patterns. These advantages are achieved by a reduction of cross-talk, since cross-talk causes the point-spread function of the lens only system (curve 320) to have larger spurious signal levels attributable to adjacent layers. Additional signal-to-noise improvement is attributable to the use of heterodyne versus direct detection. These advantages allow the use of multiple levels of signal reflectivity, that can provide multiple bits of information, at a single spatial data bit location on a disk layer. This could be implemented, for example, by varying the depth of a data-bit depression causing varying optical interference and varying reflection of the total reflected signal intensity. Alternatively, different types of partially reflective coatings or refractive index discontinuities localized to the data pixel could be applied or modified.

Figure 6:
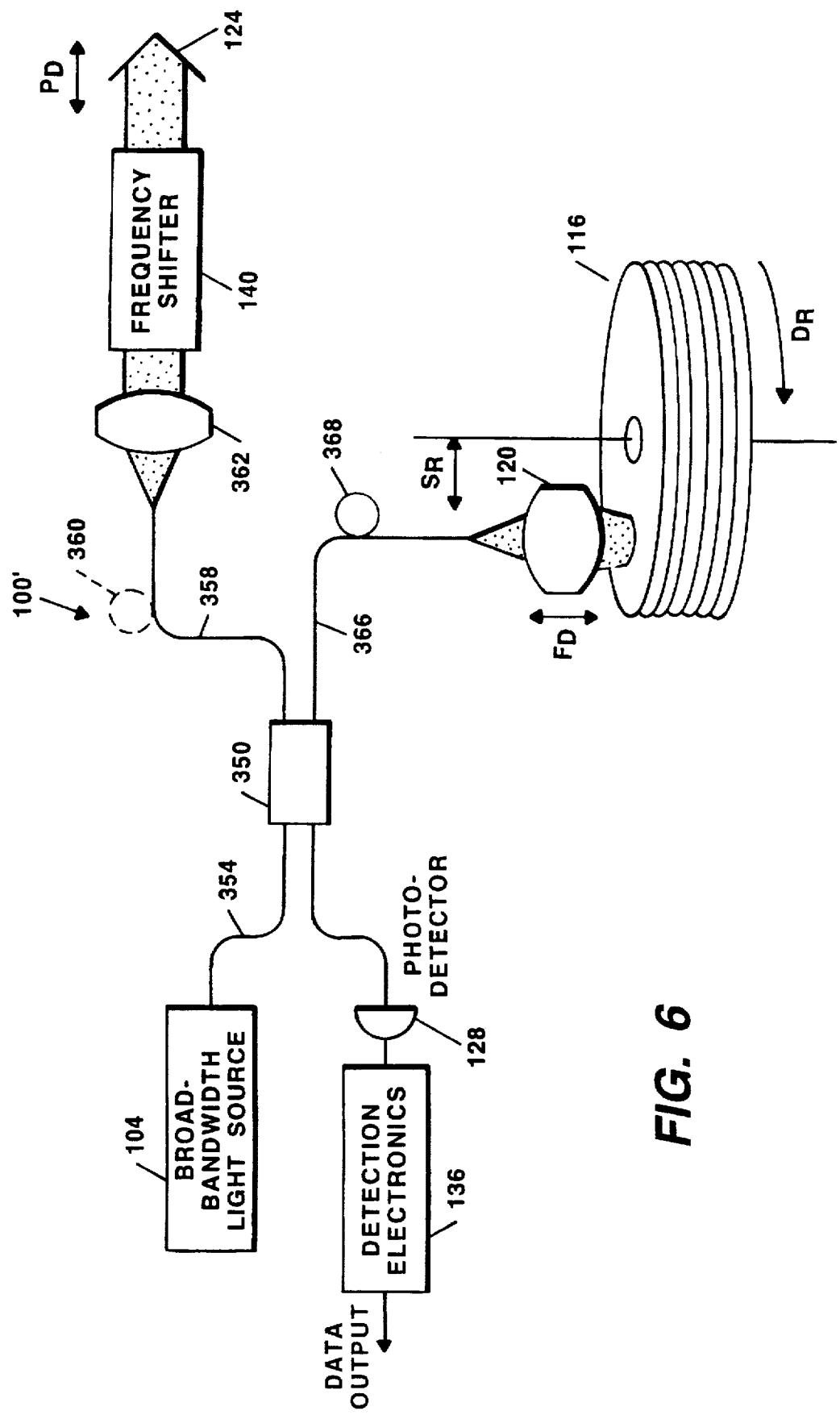
FIG. 6 is a block diagram of a further embodiment of the apparatus of the invention utilizing an interferometric technique.

Referring to FIG. 6, another interferometric embodiment of the apparatus for accessing data from a multilayered optical medium, such as an optical disk 116, includes a fiber-optic Michelson interferometer 100' and a broad bandwidth light source 104. A 50/50 optical fiber coupler 350 replaces the beam splitter 112 of the previous embodiments. Light from the broad bandwidth light source 104 is injected into one optical fiber 354 of the optical fiber coupler 350. The optical fiber coupler 350 divides the light from the light source 104 into two portions. One portion of light is transmitted by way of optical fiber 358 to a movable mirror 124. Note that a fiber stretcher 360 positioned along optical fiber 358 may replace or be used in addition to the moveable mirror 124. An illustrative fiber stretcher 360 includes a fiber wound around a PZT coil. Between optical fiber 358 and layer selection mirror 124 is a lens 362 and an optional frequency shifter 140. Alternatively, fiber-based frequency shifters may be used in place of frequency shifter 140. A second portion of light passes through optical fiber 366 to disk 116. A focusing lens 120 is used to focus light from the optical fiber 366 onto disk 116.

Light reflected by the disk 116 and light reflected by the movable mirror 124 are recombined in the fiber optic coupler 350 and form an interference pattern at detector 128. Again, when the path length of light to and from the movable mirror 124 equals the path length to and from a reflecting layer on the multilayered disk 116, an interference pattern will be generated. Therefore, as discussed previously, a given layer can be selected for access by moving the movable mirror 124 (along arrow $P_D$) or by the fiber stretcher 360.

In a fiber-based system using conventional non-polarization-maintaining fiber, the relative states of polarization of the light from the signal and reference paths which recombine in the 50/50 beam splitter 350 and mix at the photodetector 128 are not known a priori. For efficient mixing to occur at the detector 128, the two polarization states there must be the same. This can be achieved by inserting an adjustable fiber version of a quarter-wave plate/ half-wave plate polarizer 368 (which can be implemented by winding the fiber about two twistable paddles) in the signal path as shown in FIG. 6 or alternatively in the reference fiber path and by adjusting the polarizer for maximum signal.

An alternative means of ensuring maximum mixing efficiency is to employ a polarization-diversity receiver. With this method, the return signal and reference beams are decomposed into orthogonal polarization components. The like polarization components of the signal and reference beams are combined, and the combined beams having different states of polarization are mixed in different detectors, or in different portions of detector 128.

In a non-fiber system, a polarization discrimination scheme can be used with Optical Coherence Domain Reflectometry (OCDR) detection for polarization sensing of the reflected signal, which might be altered by magneto-optic rotation. Typically, the polarizing element is set to provide a signal null. In the presence of a polarization rotating data bit, the return polarization is rotated and the signal increases. With the sensitivity and dynamic range provided by OCDR detection and with the inclusion of polarizing optics, multiple (M-ary) rotation angle (signal levels) may be sensed in order to process multiple bits/pixel.

Figure 7:
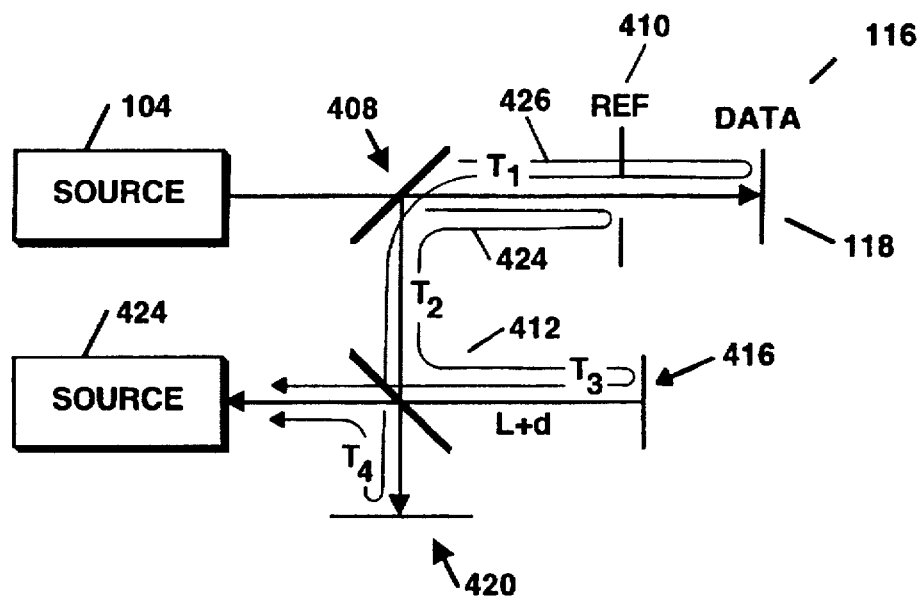
FIG. 7 is a block diagram of an interferometric embodiment of the invention including apparatus for reducing data detection errors due to jitter of the optical medium.

Referring to FIG. 7, a block diagram of another interferometric embodiment of the invention is shown to include a Fabry-Perot arrangement for enhancing data detection accuracy by counteracting effects of jitter, or movement of a multilayered optical medium, or disk 116, in a direction normal to the plane of the medium (i.e., out-of-plane jitter). The system includes a light source 104 which directs light to a beam splitter 408. The beam splitter 408 directs light along a path $T_1$ toward a reference surface 410 and multilayered optical disk 116. The reference surface 410 is fixedly coupled to the optical medium 116 and spaced therefrom by a fixed offset distance "d". All distances refer to optical path distances, with spatial distances multiplied by corresponding refractive indices. Thus, regardless of whether the disk 116 experiences out-of-plane jitter during the data access process, the distance "d" remains fixed since the reference surface 410 experiences the same jitter.

Reference surface 410 reflects a portion of incident light and permits a portion of such incident light to pass to the optical disk 116. The reference surface 410 may be implemented in various ways; for example, in one embodiment the reference surface 410 is a front surface of the optical disk 116. Other implementations of reference surface 410 include coupling the reference surface to the probe module housing the optics that move with respect to the disk and providing the reference surface metered off of the focusing lens (such as lens 132 in FIG. 4). In a fiber embodiment, such as that shown in FIG. 6, the reference surface may be provided by the end of the fiber. It will be appreciated that the reference surface 410 may alternatively be located in the source path as opposed to being disposed in the detection path, as illustrated.

Light reflected by the reference surface 410 and the layers of the disk 116 is reflected by the first beam splitter 408 along a second path $T_2$ toward a second beam splitter 412, which splits the light into a third path $T_3$ directed to a first moveable mirror 416 and a fourth path $T_4$ directed to a second mirror 420. The first moveable mirror 416 is spaced from the second beam splitter 412 by a distance "L+d" and the second mirror 420 is spaced from beam splitter 412 by a distance "L", as shown. Mirror 416 is controlled, so that interference is detected at distance "d" inside the optical medium (i.e., the distance to data layer 118). Thus, by moving mirror 416, different data layers are accessed.

In operation, a portion of the light from the source 104 travelling along path $T_1$ is reflected by the reference surface 410 and a portion of the light passes therethrough to impinge on the layers of optical disk 116. The light incident on the disk 116 is reflected at some time after the reflection from reference surface 410. The delay between such reflections corresponds to the additional path length "d", which results in a "2d" delay of the disk reflected light relative to the reference surface reflected light. The reflections from disk 116 and reference surface 410 are directed by beam splitters 408 and 412 along paths $T_3$ and $T_4$ to mirrors 416 and 420, respectively, which reflect the incident light and direct a portion of such light to a detector, such as a photodetector 424. Photodetector 424 is further coupled to processing electronics (not shown) like similar electronics 136 shown in FIGS. 2, 4 and 6.

Since the length of path $T_3$ is greater than the length of path $T_4$ by the offset "d" which can be adjusted by moveable mirror 416 and the path length to disk 116 is greater than the path length to reference surface 410 by the same offset "d", an interference pattern will be generated at the detector 424 in response to light reflected by the reference surface 410 and light reflected by the selected layer of disk 116.

With this arrangement, this reflection coincidence is independent of the distance between the disk 116 (and the reference surface fixedly coupled thereto) and the beam splitter 408 (i.e., path $T_1$), as well as the distance between the two beam splitters 408 and 412 (i.e., path $T_2$). This is because the distances associated with paths $T_1$ and $T_2$ are travelled by both of the interfering reflections and thus, cancel each other. Thus, with this arrangement, out-of-plane movement of the optical disk 116 relative to the beam splitter 408 (i.e., variations in the length of path $T_1$) does not affect the accuracy of data detection. There are other similar optical arrangements as is known in the art which may be suitable for use with the invention.

The broad bandwidth light source 104 of the interferometric embodiments of FIGS. 2, 4, 6 and 7 can provide illumination of various forms, either continuous envelope (i.e., fixed intensity) or modulated envelope (i.e., modulated intensity), each of which can be further divided into short coherence length light sources and frequency chirped light sources. Illustrative forms of light sources used to provide modulated envelope and short coherence length illumination will be described below.

In embodiments in which the light source 104 is a short coherence length light source, the detection electronics 136 operate in accordance with Optical Coherence Domain Reflectometry (OCDR). Illustrative OCDR processing electronics 136 include an amplifier for amplifying the photodetected light, a filter for increasing the signal-to-noise ratio of the detected light and an envelope detector. A comparator is provided for comparing the output of the envelope detector with a predetermined threshold to determine whether the light reflected by the selected disk layer represents a one or zero. Short coherence length light sources may take the form of a light emitting diode (LED), a superluminescent diode (SLD) or rare earth doped single-mode optical fiber.

As mentioned, the light source 104 may alternatively be a frequency chirped light source. Various conventional chirp techniques may be used to frequency chirp a laser source, or alternatively, a swept external cavity laser or other kinds of frequency swept lasers may be used. Use of a frequency chirped light source can eliminate the need for the frequency shifter 140 and moveable mirror 124, as shown in FIGS. 2 and 4, and can be used to simultaneously access all data layers of the disk 116 in a manner similar that described below in conjunction with FIGS. 8A and 8B. The difference between the use of frequency chirped light in conjunction with the embodiments of FIGS. 2, 4, 6 and 7 and the arrangement described below is that, in the former case, the processed signals are optical signals, whereas the processed signals described below in conjunction with FIG. 8B are electrical signals.

Figure 8:
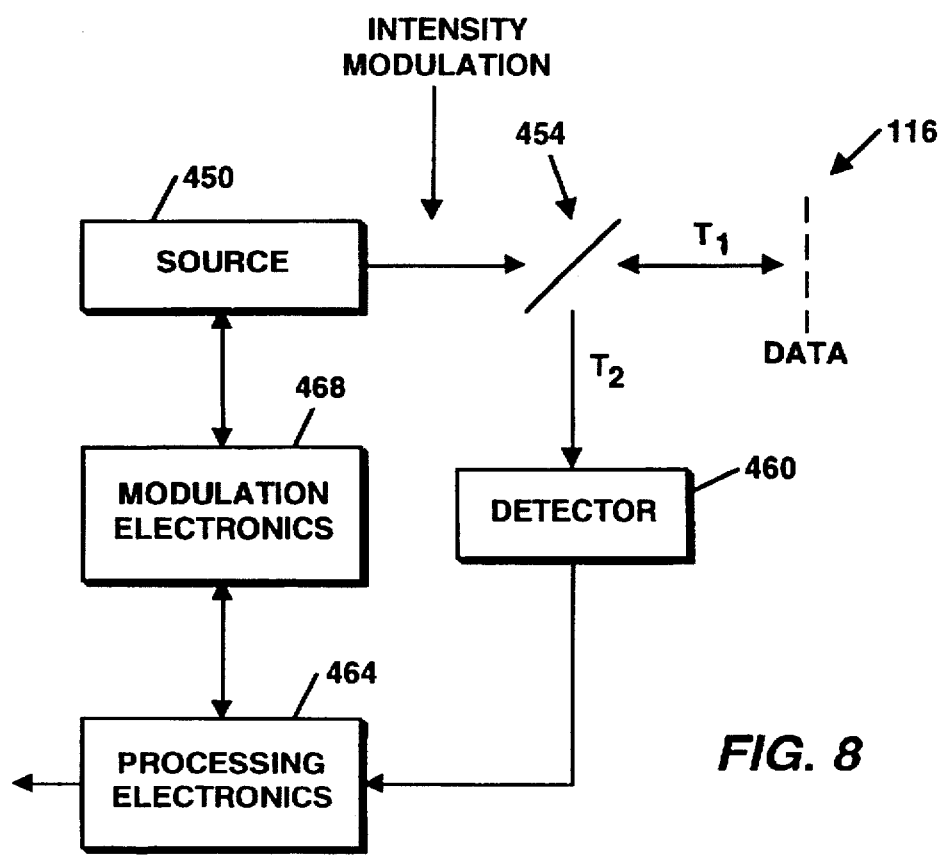
FIG. 8 is a block diagram of an embodiment of the invention utilizing a non-interferometric technique.

Referring to FIG. 8, a block diagram of a non-interferometric embodiment of the present invention is shown to include a light source 450 directing a beam of light to a beam splitter 454. The beam splitter 454 splits the light into a first path $T_1$ toward a multilayered optical medium, or disk 116. Light reflected from the disk 116 is further directed by the beam splitter 454 to a detector 460, as shown.

The detector 460 is coupled to processing electronics 464 which process the light reflected by the disk 116 and incident on the detector 460 in order to detect data stored on a selected layer of the disk 116. Modulation electronics 468 are coupled in a feedback relationship between the processing electronics 464 and the light source 450 for modulating the intensity of the light provided by the source 450. The modulation electronics 468 includes, generally, a modulation signal source. The modulation signal is used both to modulate the intensity of light provided by the source 450 and to provide an electrical reference signal to the processing electronics 464 for use in reading data from the disk 116.

The light source 450 may take various forms to provide non-continuous wave, intensity modulated illumination. Illustrative types of light sources 450 for use with the non-interferometric embodiment of FIG. 8 are pulsed light sources, in which case the processing electronics 464 are of the type used in Optical Time Delay Reflectometry (OTDR) or intensity modulated sources, such as sinusoidal or frequency chirped. These intensity modulated light sources 450 may take the form of active mode locked lasers, passive mode locked lasers, gain switched lasers or soliton compression sources. More particularly, a mode-locked laser with periodic pulse output can provide extremely short pulse widths and corresponding large spectral bandwidths. In an actively mode-locked laser, external modulation of the gain or refractive index of an element in the laser cavity forces the phase of the optical cavity modes into a fixed relation. The total electric field, comprised of the sum of these multiple modes, periodically undergoes constructive and destructive interference at a rate equal to (or a multiple of) the frequency difference between adjacent modes. The larger the number of modes contributing to this interference, the shorter the duration of constructive interference (pulse width). In a passively-mode locked laser, a non-linear element in the cavity, such as a saturable absorber or non-linear spatial focusing medium, is altered in the presence of intense fields so as to provide maximum round-trip propagation gain in the cavity for short, high-intensity pulses.

A gain-switched laser (typically a semiconductor laser) provides short pulses by means of modulation of the laser excitation in conjunction with the non-linear dynamics of the coupled gain medium and optical field. Typically, the gain medium is maintained close to the laser threshold by a continuous excitation, and a small modulation (pulsed or sinusoidal) briefly increases the gain. The optical field rapidly increases, saturating and reducing the gain, causing the optical pulse to self terminate. Unlike a mode-locked laser, there is no relation between the pulse repetition rate and the cavity round-trip frequency.

A soliton compression source generates pulses through non-linear self-phase modulation in an optical medium, such as an optical fiber. In one example, an initial optical field is comprised of two optical frequencies. The intensity of this field is modulated at the beat frequency between the two carriers. If the total modulated intensity is strong enough, as it propagates through a fiber with a non-linear index of refraction and anomalous group-velocity dispersion, the combined non-linear and dispersive effects compress the intensity wave form from a sinusoid to a narrow-duty-cycle pulse resembling an optical soliton. As this happens, the spectrum broadens from two frequencies to a band of frequencies, separated by the original beat frequency.

The processing electronics 464 selects a layer of the disk 116 to be accessed by discriminating reflections from the disk on the basis of their time-of-flight to and from the disk. More particularly, a reflection from an upper layer of the disk 116 (i.e., closer to the detection optics) will take a shorter duration to reach the detector 460 than a reflection from a lower layer (i.e., further from the detection optics). The processing electronics 464 compares the time of arrival of reflections to predetermined reference times of flight associated with the path of light to and from each of the layers of the disk 116. In this way, the processing electronics 464 discriminates between reflections from different layers and selects reflections from only the layer desired to be accessed.

The processing electronics 464 additionally includes circuitry for reading the data on the accessed disk layer. This is achieved by determining correlation of the modulation signal provided by the modulation electronics 468 and the output signal of the detector 460. Such time correlation between such signals is indicative of a first reflection type (i.e., either a "1" or a "0") and non-correlation between such signals is indicative of the second reflection type.

Figure 8A:
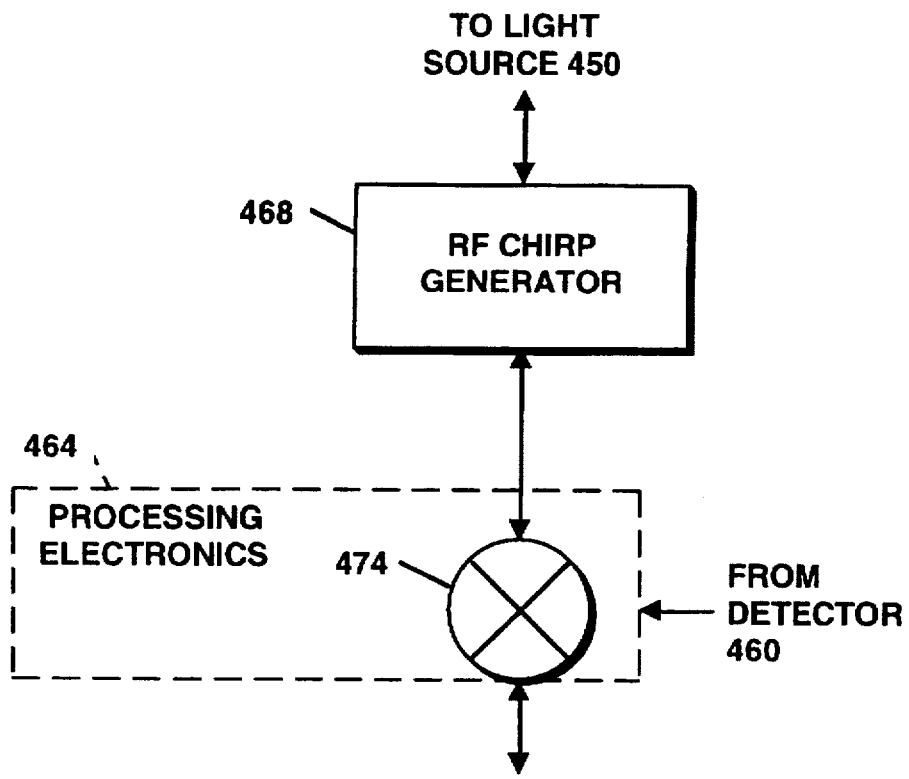
FIG. 8A is a block diagram of illustrative electronics for use in the system of FIG. 8.
Figure 8B:
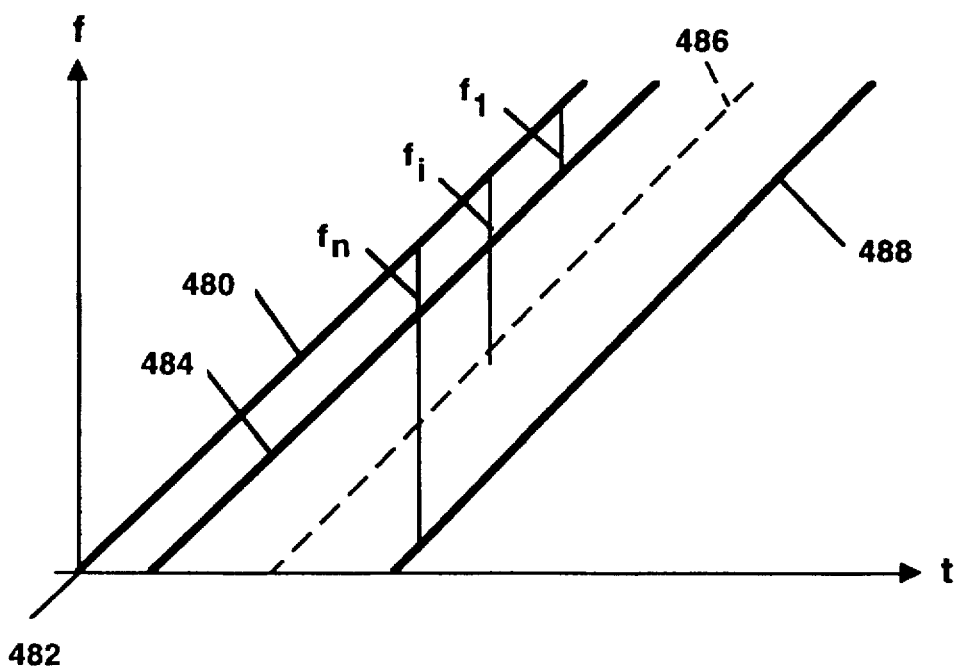
FIG. 8B is a graphical representation of the frequency versus time relationship of reflections from different layers of a multilayer medium.

Referring also to FIG. 8A, illustrative electronics are shown for use in the system of FIG. 8 when the light source 450 generates a frequency chirped signal. In this case, the modulation electronics 468 comprises an RF chirp generator 468 and the processing electronics 464 includes a mixer 474. The RF chirp generator 468 generates the modulation, or chirp signal which is provided to both the light source 450 (FIG. 8) and to the mixer 474 and which determines the time variation of the frequency of the light. The detector output signal has a frequency which varies relative to the chirp signal frequency as a function of the delay associated with travel of the light to and from the disk 116. The mixer 474 mixes the chirp signal with the detector output signal.

Referring also to FIG. 8B, the operation of the frequency chirp embodiment will be described in conjunction with an illustrative chirp signal 480 which has a linear characteristic (i.e., the frequency of the chirped light varies linearly). In this case, the frequency of the chirp signal 480 varies linearly with time, as shown, but has a fixed slope and intercept 482. The offset between the linearly varying frequency of the output of detector 460 will vary relative to the linear chirp signal 480 in accordance with the delay associated with the time it takes light to travel to the disk 116 and back to the detector 460. Stated differently, the frequency offset between the chirp signal 480 and the detector output signal is fixed and is indicative of the layer of the disk 116 which reflected the light corresponding to the detector output signal. The mixer 474 and frequency discrimination electronics determine the frequency offset between the chirp signal 480 and the output of the detector 460.

For example, signal 484 which has a fixed frequency offset of $f_1$ relative to the chirp signal 480 represents a reflection from an upper layer of the disk 116 (close to the detection optics). Signal 488 on the other hand has a greater fixed frequency offset $f_n$ relative to the chirp signal 480 and represents a reflection from a lower layer of the disk (further from the detection optics) since its time of flight is longer than that associated with signal 488.

The processing electronics 464 (FIG. 8) selects a particular layer of the disk 116 for access by processing only detector output signals with a predetermined frequency offset relative to the chirp signal which is known to be associated with reflections from the desired disk layer. The determination of whether a "1" or "0" is associated with a presently detected location of the selected layer is based on whether a signal is present at the predetermined frequency offset. For example, the dotted line 486 indicates a frequency offset $f_i$ associated with reflection from an intermediate disk layer. However, the absence of a signal at this frequency offset $f_i$ corresponds to the detection of a particular data type (i.e., either a "1" or a "0"). As is known in the art, other types of chirps are possible.

Referring to FIG. 9, an interferometric embodiment of the present invention for simultaneously accessing multiple layers of a multilayer optical medium, such as disk 116, is shown. The system includes a light source 504 which directs an illumination to an interferometric beam splitter 508. Beam splitter 508 directs a first portion of the light toward a multifocal optical element 512 positioned adjacent to the multilayer disk 116. The multifocal optical element 512 focusses the incident collimated beam at multiple colinear foci along the light path, corresponding to the multiple layers of disk 116. One illustrative multifocal optical element 512 is a holographic lens.

A second portion of the light from source 504 is directed by the beam splitter 508 toward multiple additional, reference beam splitters 516, 520 and 524. Each of the reference beam splitters 516, 520 and 524 directs incident light to a corresponding moveable reference mirror 528, 532, 536 through a respective frequency shifter 540, 544, 548. Light reflected by mirrors 528, 532, 536 and beam splitters 516, 520 and 524 passes through beam splitter 508 to impinge on a detector 550. Light reflected by the multiple layers of multilayer disk 116 is recollimated as it passes through the multifocal optical element 512 and is further reflected by the beam splitter 508 to impinge on the detector 550.

It is noted that in applications in which the separation between layers of the multilayered disk 116 is fixed and known, the multiple reference mirrors 528, 532 and 536 need not be moveable. Rather, a mechanism 542 positioned between beam splitter 508 and beam splitter 516 may be used to simultaneously vary the reference path lengths associated with each of the multiple reference paths.

The measuring path of the interferometric system of FIG. 9 is defined as the path from source 504 to disk 116, from disk 116 to beam splitter 508, and from beam splitter 508 to the detector 550. The reference path consists of multiple individual subreference paths, each with a path length adjusted to correspond to a different layer of said multilayered optical disk 116. More particularly, a first reference path is defined as the path from the source 504, through beam splitters 508 and 524, to be reflected by mirror 536 and then back through beam splitters 524 and 508 to detector 550. Similarly, a second reference path extends from the source 504, through beam splitter 508, to be reflected by beam splitter 520 and mirror 532, back through beams splitters 520 and 508 to the detector 550. Finally, an "$n_{th}$" reference path is defined as the path from the source 504, through the beam splitter 508 to reference beam splitter 516, from beam splitter 516 to respective mirror 528, back through beam splitters 516 and 508 to impinge on detector 550.

As described above in conjunction with the other interferometric systems of FIGS. 2, 4, 6 and 7, when the length of the reference path equals the length of the measuring path, an interference pattern is generated at the detector 550. In operation, the first mirror 536 is positioned to render the length of the reference path associated therewith equal to the length of the measuring path to a layer 1 of disk 116, the second mirror 532 is positioned to render the length of the reference path associated therewith equal to the length of the measuring path to layer 2 of the disk 116 and the "nth" mirror 528 is positioned to render the length of the reference path associated therewith equal to the length of the measuring path to a layer "n" of the disk 116. Thus, with this arrangement, the reference reflection from mirror 528 will generate an interference pattern at detector 550 with the reflection from layer "n" of the disk 116, the reference reflection from mirror 532 will generate an interference pattern at detector 550 with the reflection from layer 2 of the disk 116 and the reference reflection from mirror 536 will generate an interference pattern at detector 550 with the reflection from layer 1 of the disk 116.

Frequency shifters 540, 544 and 548 shift the frequency of the reference light beams in order to enhance the signal to noise ratio of the data detection. The signal generated at detector 550 is thus composed of "n" different signals having "n" different frequencies. The system additionally includes filters 544, 548 and 552 for demodulating the "n" detected signals for further processing by an envelope detector and comparator, as described above, in order to detect data stored on the disk 116.

Figure 10:
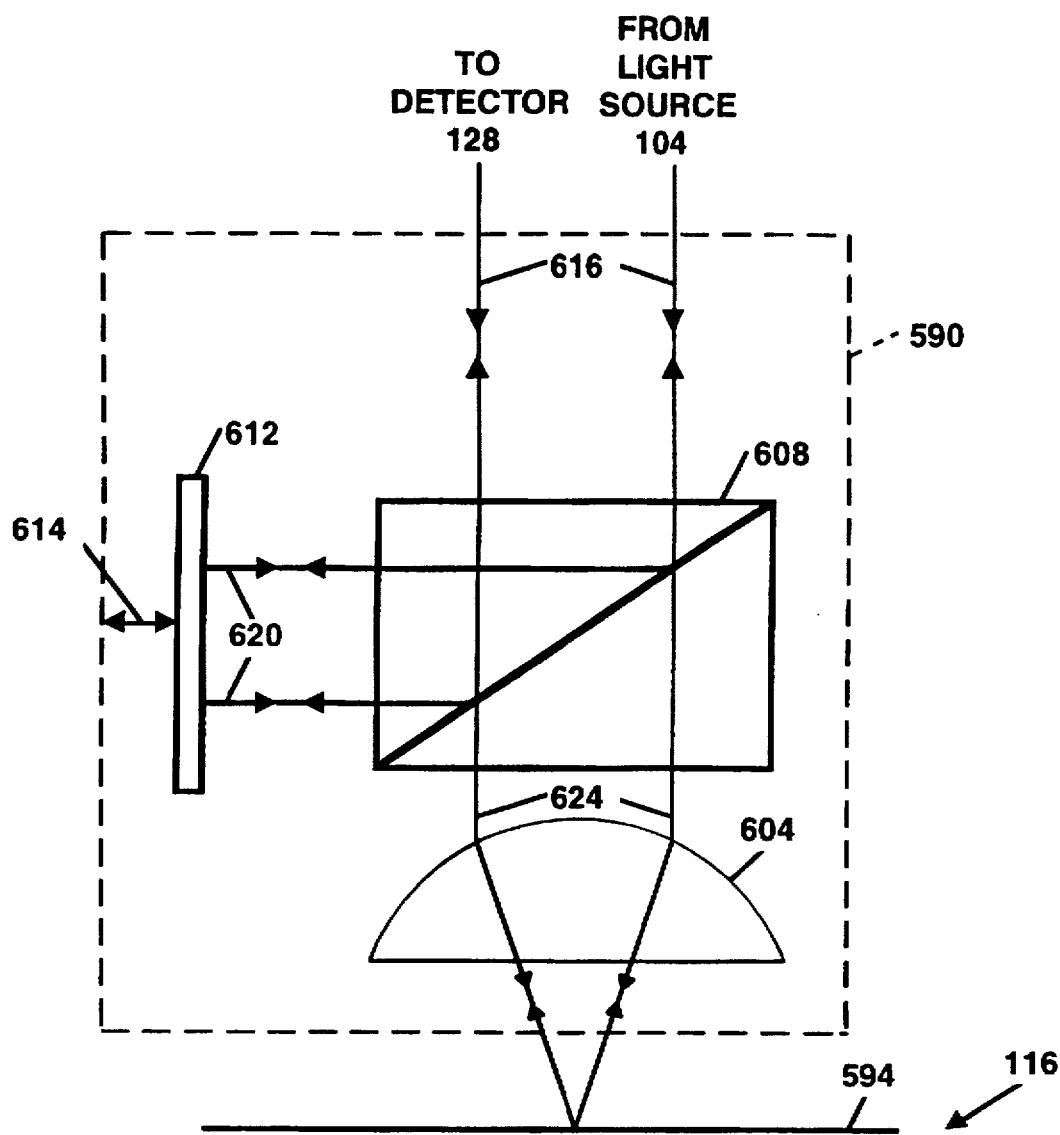
FIG. 10 is a diagram of illustrative optics for use with interferometric embodiments of the invention.

Referring to FIG. 10, an illustrative embodiment of a compact Mirau interference objective lens system, which functions similarly to the system of FIG. 4, is shown. The optics are housed in a housing, or unit 590 in which a moveable reference surface, such as a mirror 612, is also located. Preferably, the optical detection elements are integrated into a miniaturized housing 590, to provide an advantageously small optical detection system. The unit 590 of FIG. 10 is adapted for use with and connection to a light source 104, a detector 128, and processing electronics 136, all of which are shown in FIG. 4, and which are external to the unit 590. The unit 590 of FIG. 10 is adapted for accessing a selected layer 594 of a multilayered optical medium, such as disk 116.

A semireflecting surface 608 is positioned adjacent to a high numerical aperture focussing lens 604 and to the reference mirror 612. The reference mirror 612 may be moved by any suitable mechanism, such as a piezoelectric transducer, along arrow 614 in order to select a layer 594 of the disk 116 to be accessed.

In operation, a collimated light beam 616 is directed from a light source toward the semireflecting surface 608. More particularly, the collimated beam 616 may be provided by apparatus similar to that shown in FIGS. 2 and 4. In this case, light from a source 104 is collimated by a lens 108 and the collimated beam is reflected by the beam splitter 112 to provide the collimated beam 616 to the semireflecting surface 608 of FIG. 10. Alternatively, the collimated beam 616 may be provided by apparatus similar to that shown in FIG. 6, in which case divergent light is directed by the end of the fiber 366 toward a lens 120 which collimates the light to provide the collimated beam 616 to the semireflecting surface 608 of FIG. 10. It will be appreciated that where apparatus like that shown in FIGS. 2, 4 or 6 is used to provide the collimated beam 616 to the unit 590 of FIG. 10, the interferometer (i.e., moveable reference mirror 124) of FIGS. 2, 4, and 6 may be eliminated, since the unit 590 includes an interferometer.

The semireflecting surface 608 directs a first portion 620 of the incident light toward the reference mirror 612 and a second portion 624 toward the lens 604 which focusses the light onto a surface 594 of the disk 116 to be accessed. The light directed to and reflected by the disk surface 594 impinges again on the semireflecting surface 608. Similarly, the light directed to and reflected by the reference mirror 612 impinges again on the semireflecting surface 608, as shown. The reflected light incident on the semireflecting surface 608 is reflected by the surface 608 toward the detector 128. More particularly, in the case where the apparatus of FIG. 4 is used to provide the collimated beam 616 to the unit 590 of FIG. 10, the semireflecting surface 608 directs the reflected light beam to the beam-splitter 112 and detector 128 (FIG. 4). In the case where the apparatus of FIG. 6 is used to provide the collimated beam 616 to the unit 590 of FIG. 10, the semireflecting surface 608 directs the reflected light beam to the collimating lens 120 which refocuses the beam back into the fiber 366, and through beam-combiner 350 to detector 128 (FIG. 6).

The detector 128 operates to detect data on the disk surface 594 in a manner similar to that described above in conjunction with the other interferometric embodiments in that, when the reference light beam (i.e., a beam incident on and reflected by the reference mirror 612) interferes with a measured light beam (i.e., a beam incident on and reflected by selected layer 594 of the disk 116), then an interference pattern is generated at the detector 128. Further processing of the detected signal by processing electronics 136 indicates whether the reflecting disk location stores a "1" or a "0", as described above.

Having shown the preferred embodiment, those skilled in the art will realize many variations are possible which will still be within the scope and spirit of the claimed invention.

For example, and as described above, data may be stored on one or more layers of a multilayered optical medium or, alternatively may be stored on multiple layers within a unitary optical medium structure. The apparatus and techniques described above in conjunction with accessing data stored on a layer of a multilayered medium are readily adaptable for use in accessing data stored on multiple layers within a unitary optical medium structure. In the former case, the amount of illumination reflection may be indicative of the stored data, whereas in the latter case the occurrence or non-occurrence of such reflection may be indicative of the stored data.

Therefore, it is the intention to limit the invention only as indicated by the scope of the following claims.

What is claimed is:

1. A system for reading data comprising:
   a medium containing said data, said data disposed on at least one layer;
   a source of illumination, said illumination incident upon said medium; and
   a time-of-flight device for selecting said at least one layer and measuring alteration of said incident illumination caused by data on at least one layer.

2. The system of claim 1 wherein said time-of-flight detector is an interferometric detector.

3. The system of claims 2 wherein said interferometric detector is a Michelson interferometer.

4. The system of claims 2 wherein said interferometric detector is a Michelson interferometer with a variable reference path length.

5. The method of claim 2 wherein said source of illumination is a constant envelope source.

6. The system of claim 5 wherein said source of illumination is a continuous wave short coherence length source.

7. The system of claim 5 wherein said source of illumination has a frequency chirp on an optical carrier.

8. The system of claim 7 wherein said at least one predetermined layer is selected by modulating said frequency chirp on said optical carrier.

9. The system of claim 2 wherein said illumination is an intensity modulated source.

10. The system of claim 9 wherein said source of illumination is a pulsed source.

11. The system of claim 2 wherein said interferometric detector includes a frequency shifter which modulates a carrier frequency of light in one arm of said interferometric detector with respect to light in a second arm of said interferometric detector.

12. The system of claim 2 wherein said interferometer further includes a movable mirror, said mirror being movable to select said at least one predetermined layer.

13. The system of claim 1 wherein said time-of-flight detector is a non-interferometric detector.

14. The system of claim 13 wherein said non-interferometric detector is an optical time delay detector.

15. The system of claim 13 wherein said non-interferometric detector correlates the frequency of detected intensity from said data with a reference signal.

16. The system of claim 13 wherein said source of illumination is an intensity modulated source.

17. The system of claim 16 wherein said source of illumination is a pulsed source.

18. The system of claim 16 wherein said source of illumination is an intensity modulated illumination source whose modulation is frequency chirped.

19. The system of claim 1 wherein said measurement of said alteration of said incident illumination is performed on a plurality of predetermined layers simultaneously.

20. The system of claim 1 wherein said system further comprises a plurality of time-of-flight detectors and said measurement of said alteration of said incident illumination is performed on a plurality of locations on said predetermined layer simultaneously.

21. The system of claim 1 wherein said alteration of said incident illumination is selected from the group consisting of reflectivity and polarization.

22. The system of claim 1 wherein said alteration of said incident illumination has a plurality of discrete values arising from a single spatial location of said layer.

23. The system of claim 1 wherein said time-of-flight device is a Mirau interference objective lens unit.

24. The system of claim 1 wherein said medium comprises a plurality of layers and said data is disposed on said plurality of layers.

25. The system of claim 1 wherein said medium is a unitary structure and said data is disposed in a plurality of layers within said unitary medium.

26. A method of accessing data comprising the steps of:
   illuminating, with incident light, a medium containing data, said data being disposed on at least one layer;
   selecting said at least one layer in accordance with time-of-flight of said light to and from said medium; and
   detecting said data from at least one layer by detection of alteration of said incident light as altered by said data.

27. The method of claim 26 wherein said detection is performed interferometrically.

28. The method of claim 27 wherein said detection is performed with a Michelson interferometer.

29. The method of claim 27 wherein said detection is performed with a Michelson interferometer with a variable reference path length.

30. The method of claim 27 wherein said illumination is performed using a constant envelope source.

31. The method of claim 30 wherein said constant envelope source is a continuous wave short coherence length source.

32. The method of claim 30 wherein said illumination has a frequency chirp on an optical carrier.

33. The method of claim 27 wherein said illumination is performed by pulsing the intensity of said source.

34. The method of claim 27 further comprising the step of frequency shifting light in one arm of an interferometric detector with respect to a second arm of said interferometric detector.

35. The method of claim 27 further comprising the step of moving a mirror in an interferometer to select said at least one layer.

36. The method of claim 26 wherein said detection is performed non-interferometrically.

37. The method of claim 36 wherein said detection is performed by optical time delay reflectometry.

38. The method of claim 36 wherein said detection is performed by frequency correlating the detected intensity of the altered incident illumination.

39. The method of claim 26 wherein said illumination is performed by intensity modulating a source of illumination.

40. The method of claim 39 wherein the intensity of said source of illumination is pulsed.

41. The method of claim 39 wherein said illumination is performed by frequency chirp of an intensity modulation of said source.

42. The method of claim 26 wherein said at least one layer is selected using a frequency chirp of an optical carrier.

43. The method of claim 26 wherein said detecting is performed on a plurality of predetermined layers simultaneously.

44. The method of claim 26 wherein said detecting is performed on a plurality of locations on a single predetermined layer simultaneously.

45. The method of claim 26 wherein said detected alteration of said incident light is selected from the group consisting of reflectivity and polarization.

46. The method of claim 26 wherein said alteration of said incident illumination has a plurality of discrete values arising from single spatial location of said layer.

47. The method of claim 26 wherein said medium comprises a plurality of layers and said data is disposed on said plurality of layers.

48. The method of claim 26 wherein said medium is a unitary structure and said data is disposed on a plurality of layers within said unitary medium.

49. A system for accessing data comprising:

a medium containing data disposed on at least one layer;

a source of illumination, said illumination incident upon said medium; and an interferometric detector including an optical frequency shifter, said interferometric detector providing a reference path length corresponding to a predetermined layer on which said data is disposed to be accessed.

50. The system of claim 49 wherein said interferometric detector further comprises a movable mirror in a reference arm, said mirror being movable to select said predetermined layer in said medium containing data to be accessed.

51. The system of claim 49 wherein said medium comprises a plurality of layers and said data is disposed on said plurality of layers.

52. The system of claim 49 wherein said medium is a unitary structure and said data is disposed on said plurality of layers.

53. A multilayered medium for use in a data accessing system using time-of-flight detection and focussing optics, said medium comprising a plurality of layers, wherein the minimum thickness of each of said plurality of layers requires the use of both time-of-flight and focussing optics to access said layers.

54. The multilayered medium of claim 53 wherein the minimum thickness of each of said plurality of layers is less than the minimum thickness permitted by the point-spread function of the focussing optics alone.

* * * * *